US00PP15322P2

(12) United States Plant Patent
Hooijman

(10) Patent No.: US PP15,322 P2
(45) Date of Patent: Nov. 16, 2004

(54) ***HYPERICUM* PLANT NAMED 'CURACAO'**

(50) Latin Name: *Hypericum androsaemum*
Varietal Denomination: Curacao

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 10/783,423

(22) Filed: Feb. 21, 2004

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of *Hypericum* plant named 'Curacao', characterized by its upright plant habit; durable dark green-colored leaves; large light pink-colored fruits; and good postproduction longevity.

1 Drawing Sheet

Botanical classification/cultivar designation: *Hypericum androsaemum* cultivar Curacao.

BACKGROUND OF THE INVENTION

The present Invention relates to a new and distinct cultivar of *Hypericum* plant, botanically known as *Hypericum androsaemum*, commercially used as cut stems with fruits, and hereinafter referred to by the name 'Curacao'.

The new *Hypericum* is a product of a planned breeding program conducted by the Inventor in El Quinche, Pichincha, Ecuador. The objective of the breeding program was to develop cut *Hypericum* varieties with durable foliage and attractive fruit coloration.

The new cultivar originated from a cross-pollination made by the Inventor in August, 2000 of a proprietary selection of *Hypericum androsaemum* identified as Code 213, not patented, as the female, or seed, parent with a proprietary selection of *Hypericum androsaemum* identified as Code 63, not patented, as the male, or pollen, parent. The cultivar Curacao was discovered and selected by the Inventor as a flowering plant within the progeny of the stated cross-pollination in a controlled environment in El Quinche, Pichincha, Ecuador.

Asexual reproduction of the new *Hypericum* by terminal cuttings taken at El Quinche, Pichincha, Ecuador since February, 2001, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Curacao'. These characteristics in combination distinguish 'Curacao' as a new and distinct cultivar:

1. Upright plant habit.
2. Durable dark green-colored leaves.
3. Large light pink-colored rounded fruits.
4. Good postproduction longevity.

Plants of the new *Hypericum* differ from plants of the female and male parent selections in the following characteristics:

1. Plants of the new *Hypericum* are taller than plants of the female and male parent selections.
2. Plants of the new *Hypericum* and the female and male parent selections differ in fruit coloration as plants of the female parent selection have greenish brown-colored fruits and plants of the male parent selection have green-colored fruits.

Plants of the new *Hypericum* can be compared to plants of the *Hypericum* cultivar Bosapin, disclosed in U.S. Plant Pat. No. 10,993. In side-by-side comparisons conducted in El Quinche, Pichincha, Ecuador, plants of the new *Hypericum* differed from plants of the cultivar Bosapin in the following characteristics:

1. Plants of the new *Hypericum* were taller than plants of the cultivar Bosapin.
2. Plants of the new *Hypericum* had longer internodes than plants of the cultivar Bosapin.
3. Plants of the new *Hypericum* and the cultivar Bosapin differed in stem coloration.
4. Plants of the new *Hypericum* had smaller fruits than plants of the cultivar Bosapin.
5. Plants of the new *Hypericum* and the cultivar Bosapin differed in fruit coloration as plants of the cultivar Bosapin had red-colored fruits.

BRIEF DESCRIPTION OF THE PHOTOGRAPHS

The accompanying colored photographs illustrate the overall appearance of the new *Hypericum*, showing the colors as true as it is reasonably possible to obtain in colored reproductions of this type. Colors in the photographs may differ slightly from the color values cited in the detailed botanical description which accurately describe the colors of the new *Hypericum*.

The photograph at the top of the sheet comprises a side perspective view of a typical flowering stem of 'Curacao' with developing fruit.

The photograph at the bottom of the sheet comprises a side perspective view of a typical stem of 'Curacao' in fruit.

DETAILED BOTANICAL DESCRIPTION

The new *Hypericum* has not been observed under all possible environmental conditions. The phenotype may vary somewhat with variations in environment such as temperature, daylength and light intensity, without, however, any variance in genotype.

The aforementioned photographs, following observations and measurements describe plants grown in El Quinche, Pichincha, Ecuador, in an outdoor nursery and under commercial production practices. Plants were about six months old when the photograph and description were taken. During the production of the plants, day temperatures ranged from 12 to 30° C. and day temperatures ranged from 5 to 12° C. Plants were pinched about two weeks after planting. In the following description, color references are made to The Royal Horticultural Society Colour Chart, 2001 Edition, except where general terms of ordinary dictionary significance are used.

Botanical classification: *Hypericum androsaemum* cultivar Curacao.

Parentage:

*Female parent.*—Proprietary selection of *Hypericum androsaemum* identified as Code 213, not patented.

*Male parent.*—Proprietary selection of *Hypericum androsaemum* identified as Code 63, not patented.

Propagation:

*Type.*—Terminal cuttings.

*Time to initiate roots.*—About 7 to 10 days at 22 to 30° C.

*Time to produce a rooted cutting.*—About 28 to 35 days at 22 to 30° C.

*Root description.*—Fibrous, fine; color, N199A.

*Rooting habit.*—Freely branching, moderately dense.

Plant description:

*Plant form.*—Upright and somewhat outwardly spreading perennial woody shrub; erect inverted triangle.

*Growth habit.*—Vigorous. Freely basal branching; dense and bushy growth habit.

*Plant height.*—About 107 cm.

*Plant width (spread).*—About 25 cm.

*Quantity of stems per year.*—About 4.5; production of stems increases with age of plants.

*Lateral branches.*—Length: About 100 cm. Diameter: About 5 mm. Internode length: About 6.8 mm. Strength: Strong. Texture: Smooth; glabrous. Color: 194C overlain with N199D.

*Foliage description.*—Arrangement: Opposite, simple; sessile. Length: About 8.5 cm. Width: About 5.5 cm. Shape: Cordate. Apex: Acute. Base: Cordate. Margin: Entire. Durability: Durable. Texture, upper and lower surfaces: Glabrous; smooth. Venation pattern: Pinnate. Color: Developing leaves, upper surface: 137B. Developing leaves, lower surface: 146B. Fully expanded leaves, upper surface: 137A. Fully expanded leaves, lower surface: 138B. Venation, upper surface: 145A. Venation, lower surface: 143A.

Flower description:

*Flower type and habit.*—Single flowers arranged in terminal compound umbels with about 11 flowers per inflorescence. Flowers fragrant. Flowers not persistent. Flowers face upright.

*Natural flowering season.*—Summer, typically July through early September in The Netherlands; flowering period typically lasts about 60 days.

*Postproduction longevity.*—Cut stems are typically harvested when all flowers have developed fruits. Flowers last about three days on the plant. Postproduction longevity of cut stems with fruits about 14 to 18 days.

*Inflorescence height.*—About 12 cm.

*Inflorescence diameter.*—About 9 cm.

*Flower buds.*—Height: About 9 mm. Diameter: About 8 mm. Shape: Globose. Color: 13A.

*Flowers.*—Diameter: About 2.1 cm. Depth: About 1.3 cm.

*Petals.*—Quantity per flower: Typically five. Length: About 1.1 cm. Width: About 9 mm. Shape: Oval. Apex: Obtuse. Base: Attenuate. Margin: Entire. Aspect: Incurved, concave. Texture, upper and lower surfaces: Smooth, glabrous. Color: Developing and fully expanded petals, upper surface: 13A. Developing and fully expanded petals, lower surface: 13B.

*Sepals.*—Quantity per flower: Typically five. Length: About 1.2 cm. Width: About 1 cm. Shape: Ovate to rounded. Apex: Acute. Base: Rounded. Margin: Entire. Aspect: Incurved, concave. Texture, upper and lower surfaces: Smooth, glabrous. Color: Developing sepals, upper surface: 138A, towards the base, 67A. Developing sepals, lower surface: 138B, towards the base, 67A. Fully developed sepals, upper surface: 138A, towards the base, 141C. Fully developed sepals, lower surface: 138B.

*Peduncles.*—Length: About 6.5 cm. Diameter: About 2.5 mm. Orientation: Erect to about 37° from vertical. Strength: Strong. Color: 145A overlain with 176B.

*Pedicels.*—Length: About 1.5 cm. Diameter: About 1.3 mm. Orientation: Erect to about 40° from vertical. Strength: Strong. Color: 145A overlain with 176B.

*Reproductive organs.*—Stamens: Quantity per flower: About 96. Anther shape: Reniform. Anther length: About 0.9 mm. Anther color: About 16A. Pollen amount: Moderate. Pollen color: 16A to 21A. Pistils: Quantity per flower: Typically three. Pistil length: About 1 cm. Stigma shape: Rounded. Stigma color: 71A. Style length: About 4 mm. Style color: 1A. Ovary color: 1A.

*Fruits.*—Quantity per flower: One. Type: Capsule. Shape: Ovate. Length: About 1.4 cm. Diameter: About 1 cm. Texture: Smooth, glabrous. Color: 37B, towards the base, 11D.

*Seeds.*—Length: About 0.1 mm. Diameter: About 0.03 mm. Texture: Smooth, glabrous. Color: 200C.

Disease/pest resistance: Plants of the new *Hypericum* have not been observed to be resistant to pathogens and pests common to *Hypericum.*

Temperature tolerance: Plants of the new *Hypericum* have been observed to tolerate temperatures ranging from 0 to 30° C.

It is claimed:

1. A new and distinct cultivar of *Hypericum* plant named 'Curacao', as illustrated and described.

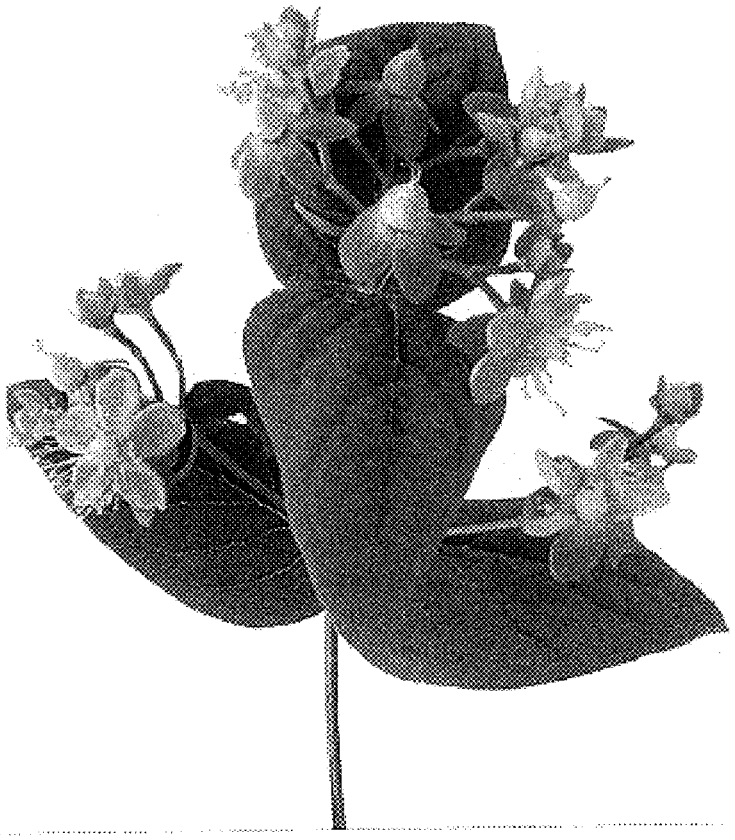
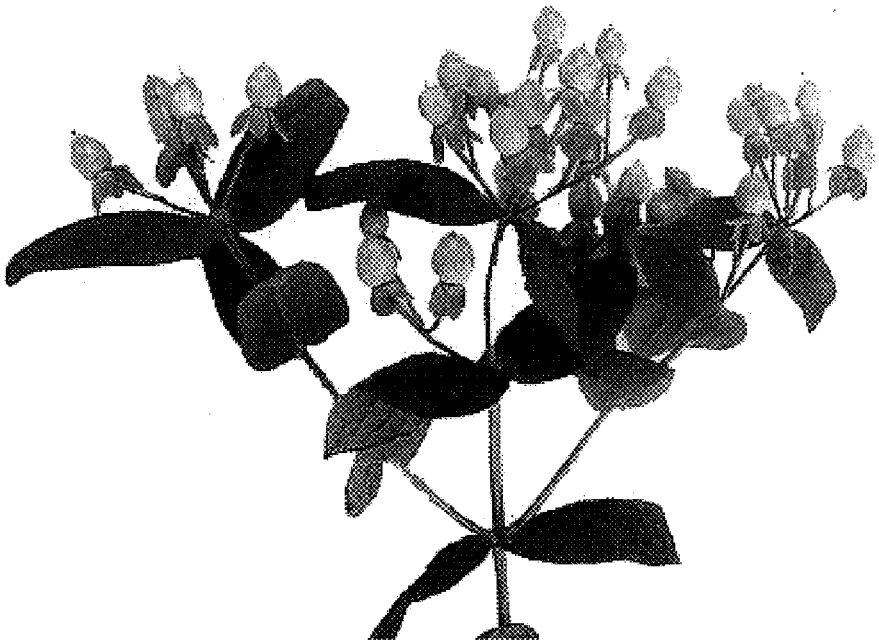

* * * * *